United States Patent [19]

Eichenberger et al.

[11] 4,185,110
[45] Jan. 22, 1980

[54] CERTAIN BENZOFURYL OR BENZOTHIENYL-2-GLYOXYLIC ACID COMPOUNDS

[75] Inventors: Kurt Eichenberger, Therwil; Hans Bosshard, Basel; Niklaus Buhler, Rheinfelden; Richard Goschke, Bottmingen; Knut A. Jaeggi, Basel, all of Switzerland

[73] Assignee: Ciba-Geigy Corporation, Ardsley, N.Y.

[21] Appl. No.: 876,380

[22] Filed: Feb. 9, 1978

[30] Foreign Application Priority Data

Feb. 11, 1977 [LU] Luxembourg ............... 76760

[51] Int. Cl.² ............... C07D 307/85; A61K 31/34
[52] U.S. Cl. ............... 424/275; 424/285; 260/346.22; 260/346.73; 260/346.73
[58] Field of Search ............... 260/346.22, 346.71, 260/346.73, 330.5; 424/275, 285

[56] References Cited

PUBLICATIONS

Dean, et al., J. Chem. Soc., 1957, pp. 3112–3117.
Fries, et al., Chem. Abstracts, 1914, pp. 3428–3429.
Mustafa, The Chemistry of Heterocyclic Compounds–Benzofurans, (vol. 29 in series), John–Wiley, 1974, p. 210.
Barton, et al., J. Chem. Soc., (1947), pp. 1574–1578.
Hart, et al., J. Chem. Soc., (1924) pp. 876–881.

*Primary Examiner*—Alan L. Rotman
*Assistant Examiner*—Bernard Dentz
*Attorney, Agent, or Firm*—John J. Maitner

[57] ABSTRACT

Novel benzoheterocyclylglyoxylic acid derivatives of the formula

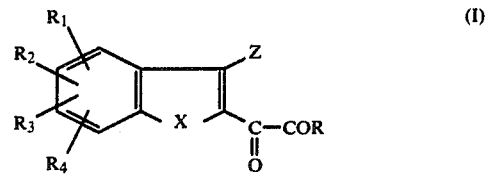

in which Z is free, etherified or acylated hydroxyl, X is thio or oxy, R is free or etherified hydroxyl, $R_1$ is lower alkyl, cycloalkyl, hydroxyl, lower alkoxy, substituted or unsubstituted phenoxy, substituted or unsubstituted amino, acyl, carboxyl, halogen, nitro or, if Z is acylated hydroxyl and/or X is oxy, hydrogen, $R_2$ is hydrogen, lower alkyl, hydroxyl or halogen and $R_3$ and $R_4$ are each hydrogen or lower alkyl, or in which two adjacent radicals $R_1$, $R_2$, $R_3$ and $R_4$ together form lower alkylene having 3 to 5 chain carbon atoms or 1,4-butadienylene and the other two radicals are each hydrogen, and their pharmaceutically acceptable salts are useful as antiallergic agents.

10 Claims, No Drawings

CERTAIN BENZOFURYL OR BENZOTHIENYL-2-GLYOXYLIC ACID COMPOUNDS

The present invention relates to benzoheterocyclyl-glyoxylic acid derivatives, especially 3-hydroxy-benzofuryl- or -benzothienyl-2-glyoxylic acid compounds of the formula

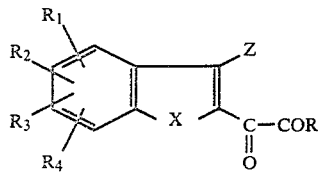

in which Z is free, etherified or acylated hydroxyl, X is thio or oxy, R is free or etherified hydroxyl, $R_1$ is lower alkyl, cycloalkyl, hydroxyl, lower alkoxy, substituted or unsubstituted phenoxy, substituted or unsubstituted amino, acyl, carboxyl, halogen, nitro or, if Z is acylated hydroxyl and/or X is oxy, hydrogen, $R_2$ is hydrogen, lower alkyl, hydroxyl or halogen and $R_3$ and $R_4$ are each hydrogen or lower alkyl, or in which two adjacent radicals $R_1$, $R_2$, $R_3$ and $R_4$ together form lower alkylene having 3 to 5 chain carbon atoms or 1,4-butadienylene and the other two radicals are each hydrogen, or salts of compounds of the formula I in which R is hydroxyl, and to processes for their preparation and also to pharmaceutical compositions containing the compounds of the formula I or salts thereof and the use of these compounds.

In this specification, the term "lower" used to qualify organic radicals and compounds denotes that these contain not more than 7, preferably not more than 4, carbon atoms.

Etherified hydroxyl is, for example, hydroxyl etherified by an aromatic, araliphatic, cycloaliphatic or, in particular, aliphatic alcohol, such as substituted or unsubstituted phenoxy, phenyl-lower alkoxy, $C_5$–$C_8$-cycloalkoxy, $C_5$–$C_8$-cycloalkyl-lower alkoxy, lower alkenyloxy or, in particular, lower alkoxy. Substituents of phenoxy or phenyl groups are in particular lower alkyl, lower alkoxy, halogen and/or nitro. Substituents of a lower alkoxy group R are hydroxyl or lower alkoxy and one or more substituents can be present.

Substituted or unsubstituted phenoxy is, for example, phenoxy substituted by lower alkyl, lower alkoxy, halogen and/or nitro.

Substituted or unsubstituted amino is, for example, amino which is unsubstituted or substituted by lower alkyl, alkylene or 3-aza-, 3-oxa- or 3-thia-alkylene having in each case 4 to 7, in particular 4–6, ring members or by acyl.

Amino substituted by lower alkyl is preferably mono- or di-$C_1$-$C_4$-alkylamino, such as methyl- or dimethyl-amino, ethyl- or diethyl-amino, methylethylamino, propyl- or isopropyl-amino or butylamino.

Amino substituted by alkylene or 3-aza-, 3-oxa- or 3-thia-alkylene of the said type is, for example, pyrrolidino, piperidino, morpholino, thiomorpholino, piperazino or $N'$-$C_1$-$C_4$-alkyl-piperazino, such as $N'$-methylpiperazino.

Amino substituted by acyl is, for example, monoacylamino which contains, as the acyl group, one of the acyl groups defined below, preferably lower alkanoylamino, such as acetylamino.

Acylated hydroxy is, for example, acyloxy which contains one of the acyl groups defined below, preferably lower alkanoyloxy, such as acetoxy, propionyloxy, butyryloxy, isobutyryloxy or pivaloyloxy.

Acyl is, for example, acyl derived from an organic carboxylic acid, preferably an aliphatic or aromatic carboxylic acid, such as lower alkanoyl which is unsubstituted or phenylsubstituted, in particular in the α-position, or, less preferentially, benzoyl or pyridinecarbonyl; the phenyl and pyridyl radicals can in each case be substituted by lower alkyl, lower alkoxy, halogen and/or nitro. Examples of preferred radicals are: acetyl, propionyl, butyryl, isobutyryl, valeroyl, pivaloyl, benzoyl and 2- and 4-chlorobenzoyl, 2,4- and 2,6-dichloro-benzoyl, nicotinoyl, isonicotinoyl and picolyl.

Lower alkoxy is, for example, methoxy, ethoxy, n-propoxy, isopropoxy, n-butoxy, isobutoxy, tert.-butoxy, n-pentyloxy or n-hexyloxy.

Hydroxy- or lower alkoxy-lower alkoxy is especially 2- and/or 3-hydroxy-lower alkoxy, for example 2-hydroxyethoxy, 3-hydroxypropoxy or 2,3-dihydroxy-propoxy, or 2- or 3-lower alkoxy-lower alkoxy, for example 2-methoxyethoxy, 2-ethoxy-ethoxy or 3-methoxypropoxy.

Lower alkyl is, for example, methyl, ethyl, n-propyl, isopropyl, n-butyl, tert.-butyl or n-pentyl.

Cycloalkyl contains preferably 5 to 8 and in particular 6 ring atoms and is, for example, cyclopentyl, cyclohexyl, cycloheptyl or cyclooctyl.

Halogen is especially halogen having an atomic number of not more than 35, i.e. flourine, chlorine or bromine.

Lower alkylene formed by two adjacent radicals $R_1$, $R_2$, $R_3$ and $R_4$ is especially 1,3-propylene or 1,4-butylene and also 1,5-pentylene. The two groups forming an alkylene radical are preferably in the 5- and 6-position.

1,4-Butadienylene formed by two of the radicals $R_1$, $R_2$, $R_3$ and $R_4$ is preferably a substituent in the 4- and 5-positions.

Salts of compounds of the formula I in which R is hydroxyl are salts with bases, in particular corresponding pharmaceutically acceptable salts, such as alkali metal or alkaline earth metal salts, for example sodium, potassium, magnesium or calcium salts, and also ammonium salts with ammonia or amines, such as lower alkyl-amines or hydroxy-lower alkylamines, for example trimethylamine, triethylamine or di-(2-hydroxyethyl)-amine.

The compounds of the formula I can also be in the tautomeric (desmotropic) 3-oxo form

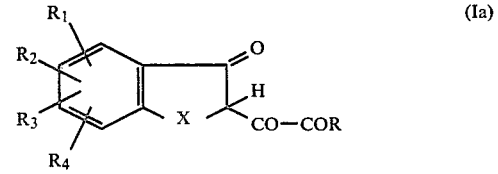

The novel compounds have valuable pharmacological properties. In particular, they have antiallergic actions which can be demonstrated, for example, in rats in doses of about 1 to about 20 mg/kg on intravenous administration and in doses of about 10 to about 100 mg/kg on oral administration in the passive cutaneous anaphylaxis test (PCA reaction), which is carried out analogously to the method described by Goose and Blair, Immunology, Vol. 16, pg. 749 (1969), the passive cutaneous anaphylaxis being produced by the procedure described by Ovary, Progr. Allergy, Vol. 5, pg. 459 (1958). The compounds of the present invention are useful as inhibitors of allergic reactions, for example in the treatment and prophylaxis of allergic diseases, such as asthma, both extrinsic and intrinsic asthma, or other allergic diseases, such as hay fever, conjunctivitis, urticaria and eczema.

The invention relates in particular to compounds of the formula I in which Z is as defined, X is thio or, less preferentially, oxy, R is hydroxyl, lower alkoxy having not more than 4 carbon atoms, hydroxy-lower alkoxy having not more than 4 carbon atoms, in which the two oxygen atoms are separated by 2 to 3 carbon atoms, or lower alkoxy-lower alkoxy having not more than 7 carbon atoms, in which the two oxygen atoms are separated by 2 to 3 carbon atoms, $R_1$ is lower alkyl having not more than 4 carbon atoms, cyclohexyl, hydroxyl, lower alkoxy having not more than 4 carbon atoms, carboxyl, lower alkanoyl, for example acetyl, lower alkanoylamino, for example acetylamino, N,N-di-lower alkylamino, for example dimethylamino or diethylamino, halogen having an atomic number of not more than 35, nitro or, if Z is acylated hydroxyl and/or X is oxy, hydrogen, and $R_2$ is hydrogen or lower alkyl, or two of the radicals $R_1$, $R_2$, $R_3$ and $R_4$ together form lower alkylene having 3 to 5 chain carbon atoms and are a substituent in the 5- and 6-positions or form 1,4-butadienylene and are a substituent in the 4- and 5-positions, and the other two radicals are hydrogen, and salts of such compounds in which R is hydroxyl, especially corresponding pharmaceutically acceptable salts.

The invention relates especially to compounds of the formula

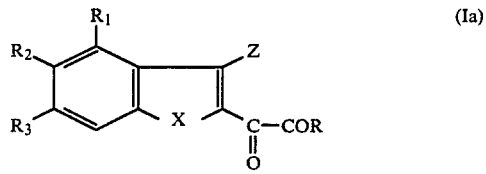

(Ia)

in which Z is hydroxyl or lower alkanoyloxy, for example acetoxy or pivaloyloxy, X is thio or, less preferentially, oxy, R is hydroxyl or lower alkoxy having not more than 4 carbon atoms, for example methoxy or ethoxy, hydroxy-lower alkoxy having not more than 4 carbon atoms, in which the two oxygen atoms are separated by 2 to 3 carbon atoms, for example 2-hydroxyethoxy or 2,3-dihydroxypropoxy, or lower alkoxy-lower alkoxy having not more than 4 carbon atoms, in which the two oxygen atoms are separated by 2 to 3 carbon atoms, for example 2-methoxyethoxy, $R_1$ is hydrogen or lower alkyl having not more than 4 carbon atoms, for example methyl, $R_2$ is hydrogen, lower alkyl having not more than 4 carbon atoms, for example methyl, or nitro, $R_3$ is hydrogen, lower alkyl having not more than 4 carbon atoms, for example methyl, hydroxyl or lower alkoxy having not more than 4 carbon atoms, for example methoxy, and only one of the radicals $R_2$ and $R_3$ differs from hydrogen or lower alkyl, or $R_1$ and $R_2$ together form 1,4-butadienylene and $R_3$ is hydrogen, or $R_1$ is hydrogen and $R_2$ and $R_3$ together form lower alkylene having 3 or 4 chain carbon atoms, for example 1,3-propylene, and $R_1$ is as defined, and at least one of the radicals $R_1$, $R_2$ and $R_3$ differs from hydrogen when X is thio and R is hydroxyl, and salts of such compounds in which R is hydroxyl, expecially corresponding pharmaceutically acceptable salts.

The invention relates in particular to compounds of the formula Ia in which Z is hydroxyl, X is thio or oxy, R is hydroxy or lower alkoxy having not more than 4 carbon atoms, for example methoxy or ethoxy, and $R_1$, $R_2$ and $R_3$ are each hydrogen, methoxy or methyl, or $R_2$ and $R_3$ together form lower alkylene having 3 or 4 chain carbon atoms, for example 1,3-propylene or 1,4-butylene, and $R_1$ is as defined, and at least one of the radicals $R_1$, $R_2$ and $R_3$ differs from hydrogen when X is thio and R is hydroxyl, and specifically those compounds of the formula Ia in which Z is hydroxyl, X is thio, R is hydroxyl or lower alkoxy having not more than 4 carbon atoms, for example methoxy or ethoxy, $R_1$ is hydrogen and $R_2$ and $R_3$ are lower alkyl having not more than 4 carbon atoms or together are 1,3-propylene, and salts of such compounds in which R is hydroxyl, especially corresponding pharmaceutically acceptable salts.

The compounds of the formula I are prepared in a manner which is known per se, for example by hydrolysing a compound of the formula

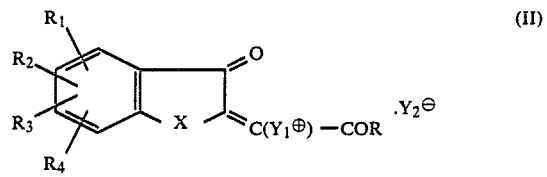

(II)

in which $Y_1^\oplus$ is an onium group and $Y_2^\ominus$ is the anion radical of an acid, and, if desired, converting a resulting compound of the formula I into another compound of the formula I and/or, if desired, converting a resulting salt into the free compound or into another salt and/or converting a resulting compound of the formula I in which R is hydroxyl into a salt.

In a starting material of the formula II, which customarily is formed in situ, an onium group is understood as meaning a positively charged group, the free valency of which emanates from the positively charged hetero-atom, especially a nitrogen atom or also a sulphur atom.

The radical $Y_1^\oplus$ is preferably an ammonium group in which the nitrogen atom can be unsubstituted or mono-, di- or tri-substituted by monovalent or divalent substituents. Such substituents are especially those of aliphatic character, such as substituted or unsubstituted monovalent or divalent aliphatic and also cycloaliphatic, cycloaliphatic-aliphatic or araliphatic hydrocarbon radicals, in particular lower alkyl or lower alkylene, in which carbon atoms can be replaced by hetero-atoms, such as oxygen atoms, or nitrogen atoms which can be unsubstituted or substituted, for example by lower alkyl, such as methyl, for example methyl, ethyl, 3-oxa-n-butyl, 1,4-butylene, 1,5-pentylene, 3-oxa-1,5-pentylene or '3-methyl-3-aza-1,5-pentylene, and also cycloalkyl, for example cyclohexyl, or phenyl-lower alkyl, for example benzyl. Preferred ammonium groups $Y_1^\oplus$ are those of the formula

 (IIa)

in which $R_a$ and $R_b$ are hydrogen or preferably lower alkyl, for example methyl or ethyl, or together form lower alkylene, in which one carbon atom can be replaced by an oxygen atom or an unsubstituted or substituted, for example lower alkylated, nitrogen atom, for example 1,5-pentylene, 3-oxa-1,5-pentylene or 3-methyl-3-aza-1,5-pentylene. An example of a possible further substituent on the nitrogen atom in an ammonium group is an amidino group; therefore, in the above partial formula IIa, $R_a$ can also be, for example, amidino and $R_b$ can be hydrogen.

Further onium groups $Y_1 \oplus$ are sulphonium groups, which, for example, are substituted by monovalent or divalent substituents of aliphatic character, such as those mentioned above, especially by lower alkyl or lower alkylene, in which carbon atoms can be replaced by hetero-atoms, such as oxygen or by nitrogen atoms which are unsubstituted or substituted, for example by lower alkyl, such as methyl, for example methyl, ethyl, 1,4-butylene or 1,5-pentylene, and preferably contain a S-oxido group. Such groups are in particular those of the formula

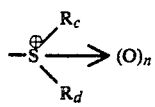 (IIb)

in which $R_c$ and $R_d$ are lower alkyl, for example methyl, or together form lower alkylene, for example 1,4-butylene or 1,5-pentylene, and n is O or preferably 1.

Anion radicals $Y_2 \ominus$ of acids are in particular those of strong acids, such as inorganic acids, for example of a hydrogen halide acid, such as hydrochloric acid and also hydrobromic acid, or sulphuric acid, or of strong organic carboxylic or sulphonic acids. The anion $Y_2 \ominus$ is therefore in particular a halogen anion, especially the chlorine anion.

The hydrolysis is preferably carried out in an acid medium, especially by treatment with a dilute acid, such as a mineral acid, for example a hydrogen halide acid, such as hydrochloric acid or hydrobromic acid, and also sulphuric acid. The hydrolysis can be carried out in the presence of an organic, preferably water-miscible, solvent or diluent, if necessary with cooling or warming (for example in a temperature range of about 10°C to about 100°C), in a closed vessel and/or in an inert gas atmosphere.

The starting material of the formula II can be obtained, for example, when a phenol or thiophenol compound of the formula

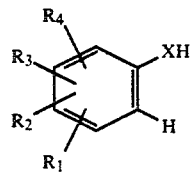 (III)

is reacted with a 2,3-di-Y-maleic anhydride in which Y is a reactive esterified hydroxyl group, for example with a 2,3-dihalogeno-maleic anhydride, especially 2,3-dichloro-maleic anhydride, by treatment with a condensing agent, for example in the presence of a Lewis acid, for example aluminum chloride, when phenols of the formula III are used as the starting material and, for example, of a base, such as an alkali metal hydroxide, for example sodium hydroxide, when thiophenols of the formula III are used as the starting material, and a condensation product which is thus obtainable, for example compounds of the formula

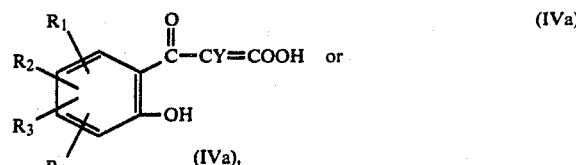 (IVa)

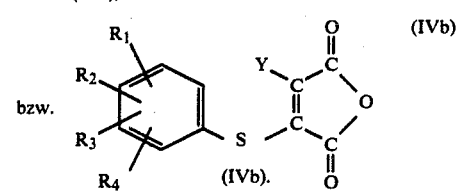 (IVb)

in which Y is as defined and in particular is halogen, especially chlorine, is cyclised by treatment with a condensing agent, such as a base, such as an alkali metal hydroxide, for example sodium hydroxide, when compounds of the formula IVa are used as the starting material and, for example, in the presence of a Lewis acid, for example aluminium chloride, when compounds of the formula IVb are used as the starting material, to give a compound of the formula

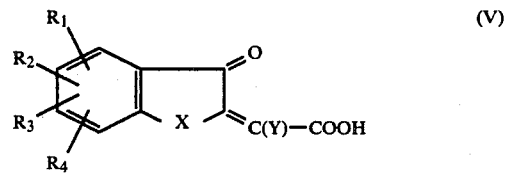 (V)

In the above starting material of the formula II, the radicals $R_1$, $R_2$, $R_3$ and $R_4$ are as defined above except that $R_1$ is not nitro; a lower alkoxy group $R_1$ can be converted into hydroxyl under the reaction conditions of the Friedel-Crafts reaction and, if desired, reconverted into a lower alkoxy group by alkylation.

In an intermediate of the formula V, obtainable by the above process, the free carboxyl group can be esterified, for example by treating the acid of the formula V with a substituted or unsubstituted lower alkanol in the presence of an acid or of a condensing agent or, in order to form a hydroxy-lower alkyl ester, with an epoxy-lower alkane, or by reacting an alkali metal salt of the acid with a substituted or unsubstituted lower alkyl halide or di-lower alkyl sulphate, or by treating the corresponding acid chloride with a substituted or unsubstituted lower alkanol, for example in the presence of a basic agent. Substituents in an esterifying reagent can be in a functionally modified form and then set free in the esterified intermediate. Thus, for example, 2,3-epoxy-propyl chloride can be used as the esterifying reagent and the 2,3-epoxy-propyl grouping in the resulting ester can subsequently be hydrolysed to the desired 2,3-dihydroxy-propyl grouping. Furthermore, a nitro group can be introduced into the carbocyclic-aromatic part of the ring system, for example by treatment with nitric acid, in the presence of sulphuric acid, or a free phenolic hydroxyl group in this ring system can be converted into a lower alkoxy group, for example by treatment with a di-lower alkyl sulphate in the presence of a base, for example potassium carbonate.

In an intermediate of the formula V, the group Y can be converted in a manner known per se into the onium group $Y_1^\oplus$ of the starting material of the formula II, the starting material customarily being formed in situ. Thus, a compound of the formula V can be treated with ammonia or an amine, for example a compound of the formula $R_a$—NH—$R_b$ (VI), and the desired ammonium group $Y_1^\oplus$ can then be formed, if necessary, by treatment with an acid and in some cases also in the acid medium of the hydrolysis reaction according to the invention. Analogously, an intermediate of the formula V can be treated with a sulphoxide or a sulphide, for example of the formula

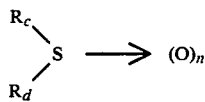

and the desired starting material of the formula II, in which $Y_1^\oplus$ is a sulphonium group, thus obtained.

The compounds of the formula I can also be prepared by reacting a starting material of the formula

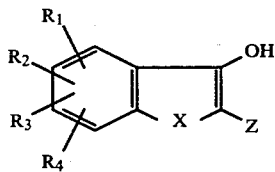

in which Z is a free or esterified carboxyl group, for example of the formula —COR, such as carboxyl or lower alkoxycarbonyl, for example methoxycarbonyl or ethoxycarbonyl, or in particular hydrogen, with an oxalic acid ester, for example of the formula RCOCOR, and, in the resulting condensation product of the formula

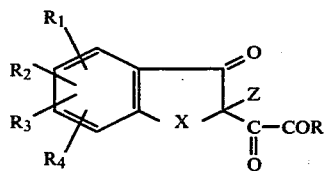

if necessary saponifying an esterified carboxyl group Z to carboxyl and/or decarboxylating carboxyl Z and, if desired, converting a resulting compound of the formula I into another compound of the formula I and/or if desired, converting a resulting salt into the free compound or into another salt and/or converting a resulting compound of the formula I, in which R is hydroxyl into a salt.

The reaction can be carried out in a conventional manner, for example in the presence of a condensing agent, such as an acid or preferably basic condensing agent, if necessary in an inert, preferably polar, solvent. Examples of acid condensing agents are proton-acids, such as mineral acids, for example hydrogen halide acids, such as hydrochloric acid or hydrobromic acid, sulphuric acid or phosphoric acid, organic sulphonic acids, such as p-toluenesulphonic acid, or carboxylic acids, such as acetic acid or trifluoroacetic acid. Examples of basic condensing agents are alkali metal hydroxides, alkali metal alcoholates, alkali metal carboxylates, alkali metal amides and alkali metal hydrocarbon compounds, such as sodium hydroxide or potassium hydroxide, sodium lower alkanolates or potassium lower alkanolates, for example sodium methylate or sodium ethylate, sodium acetate, sodium amide or tritylsodium. Examples of polar inert solvents are carboxylic acid anhydrides, for example acetic anhydride, alcohols, such as lower alkanols, for example methanol or ethanol, or ethers, for example diethyl ether, tetrahydrofurane or dioxane, or mixtures thereof.

The starting materials of the formula VI are known or can be prepared by conventional methods.

Compounds of the formula VI in which Z is hydrogen can be prepared, for example, by cyclising a compound of the formula

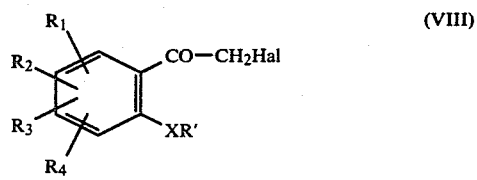

in which Hal is halogen, for example bromine, and R' is hydrogen or acyl, such as lower alkanoyl, for example acetyl, or esterified oxalo of the formula —COCOR, by the action of a base, for example of sodium hydroxide or potassium carbonate. If the starting materials are compounds of the formula VIII in which R' is a group —COCOR, the starting material of the formula VI which is first formed further reacts according to the invention, without isolation, with the compound containing the oxalic acid radical containing the group —COCOR detached during the cyclisation. With this variant, potassium carbonate in acetone is preferably used as the condensation medium. The starting materials of the formula VII are, in turn, accessible by halogenation of the corresponding o-acyloxy- or o-acylthio-acetophenone or by the action of aluminium chloride on corresponding phenyl halogenoacetates or phenyl halogenothioacetates.

Starting materials of the formula VI in which Z is free or esterified carboxyl can be prepared, for example, by subjecting a corresponding, free or esterified, o-carboxyphenoxy- or o-carboxyphenylthio-acetic acid to a condensation reaction under basic conditions and, if desired, saponifying the resulting ester.

The compounds of the formula I can also be prepared by subjecting a compound of the formula

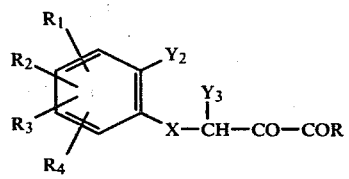

in which one of the radicals $Y_2$ and $Y_3$ is a free or functionally modified carboxyl group and the other is hydrogen, or a salt thereof to an intramolecular condensation and, if desired, converting a resulting compound of the formula I into another compound of the formula I and/or, if desired, converting a resulting salt into the free compound or into another salt and/or converting a resulting compound of the formula I in which R is hydroxyl, into a salt.

Functionally modified carboxyl groups are, for example, cyano groups or oxo group-containing functionally modified carboxyl groups, in particular esterified carboxyl groups, such as lower alkoxycarbonyl, for example methoxycarbonyl or ethoxycarbonyl. Salts of compounds of the formula IX are especially alkali metal salts, such as sodium or potassium salts, of compounds of the formula IX in which $Y_2$, $Y_3$ and/or —COR is carboxyl.

The intramolecular condensation is carried out in a conventional manner, for example by the action of heat, for example at about 60° to 300° C., and/or by treatment with a base, for example with an alkali metal hydroxide, alcoholate, amide or carboxylate, such as sodium hydroxide or potassium hydroxide, sodium ethanolate or sodium methanolate, sodium amide or lithium diisopropylamide, or sodium acetate, if necessary in an inert solvent, for example in benzene, toluene, a xylene, dimethylformamide or acetic anhydride.

In a preferred embodiment of the above process, for example, a compound of the formula IX in which $Y_2$ is esterified carboxyl and $Y_3$ is hydrogen, is treated with an alkali metal lower alkanolate, preferably with sodium methanolate or sodium ethanolate, in benzene or toluene, the reaction preferably being carried out at about 60° to 130° C., for example at 80°–100° C.

In a modification of this process, it is also possible to use the corresponding nitrile, i.e. a compound of the formula IX in which $Y_2$ or $Y_3$ is cyano, as the starting material. In this case the corresponding compound of the formula

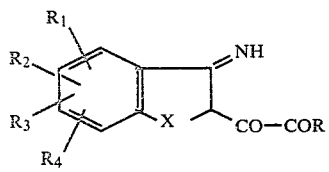

(IXa)

is first obtained as an intermediate which can be isolated and the NH group of which is hydrolysed to oxo under the conditions of the work-up.

If they are not already known, the starting materials of the formula IX can be prepared by methods known per se.

For example, compounds of the formula IX in which $Y_2$ is hydrogen and $Y_3$ is free or esterified carboxyl can be prepared by subjecting a compound of the formula

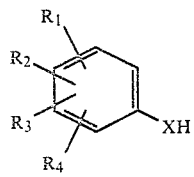

(X)

or an alkali metal salt, for example the sodium salt thereof, to a condensation reaction with a haolgeno-oxaloacetate, for example with ethyl bromo-oxaloacetate, in a conventional manner and, if necessary, hydrolysing an esterified carboxyl group $Y_3$ to carboxyl.

Compounds of the formula IX in which $Y_2$ is free or functionally modified carboxyl and $Y_3$ is hydrogen can be obtained, for example, by reacting a compound of the formula

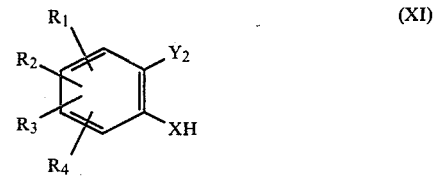

(XI)

or an alkali metal salt, for example the sodium salt thereof, with a halogenopyruvate, for example with a bromopyruvate, in a conventional manner and, if desired, hydrolysing the reaction product to the acid.

The compounds of the formula I in which X is thio can also be prepared by reacting a compound of the formula

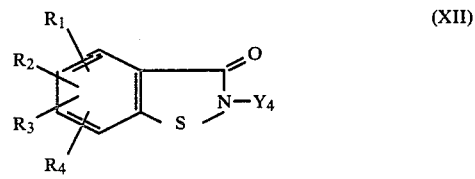

(XII)

in which $Y_4$ is a sulphonyl group with a compound of the formula $CH_3$—CO—COR or a salt thereof and, if desired, converting a resulting compound of the formula I into another compound of the formula I and/or, if desired, converting a resulting salt into the free compound or into another salt and/or converting a resulting compound of the formula I in which R is hydroxyl into a salt.

A sulphonyl group $Y_4$ is, for example, a sulphonyl group derived from an organic sulphonic acid, for example from an aliphatic or aromatic sulphonic acid, such as methanesulphonyl, ethanesulphonyl, ethenesulphonyl, p-bromobenzenesulphonyl, p-toluenesulphonyl or, in particular, benzenesulphonyl.

The reaction is carried out in a conventional manner, if necessary in the presence of a basic condensing agent, for example of an alkali metal hydroxide, such as sodium hydroxide or potassium hydroxide, or of an organic nitrogen base, such as pyridine or piperidine, and/or in an inert solvent, for example a lower alkanol, such as ethanol, or in benzene, toluene or pyridine, advantageously with warming, for example at about 50°–150° C., for example at the boil.

The starting materials of the formula XII are known or, if they are new, can be prepared according to methods known per se, for example by first reacting a compound of the formula

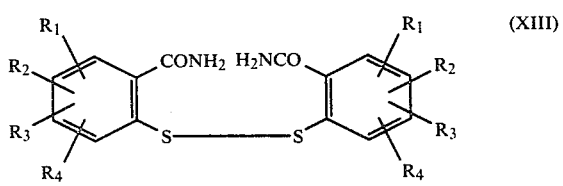

(XIII)

with bromine, preferably in carbon tetrachloride, and subsequently heating the reaction product in glacial acetic acid and reacting the compound of the formula

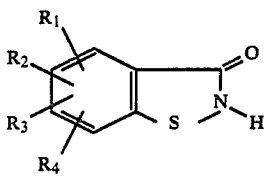
(XIV)

which is thus obtainable, in a conventional manner, for example in pyridine or, in the form of the sodium salt, in benzene, with the corresponding sulphonyl chloride or the formula Y$_4$—Cl. However, it is also possible to react a compound of the formula

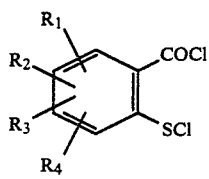
(XV)

in a conventional manner with a compound of the formula Y$_4$—NClNa or Y$_4$—NCl$_2$ and thus to obtain the desired starting material direct.

The compounds of the formula I in which X is thio can also be prepared by treating a mixture of a compound of the formula

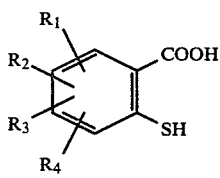
(XVI)

or of the corresponding disulphide and a compound of the formula Y$_5$—CH$_2$—CO—COR (XVII), in which Y$_5$ is hydrogen, an acyl group or carboxyl, with a mineral acid and, if desired, converting a resulting compound of the formula I into another compound of the formula I and/or, if desired, converting a resulting salt into the free compound or into another salt and/or converting a resulting compound of the formula I in which R is hydroxyl into a salt.

A disulphide of a compound of the formula XVI is to be understood as meaning the corresponding 2,2-dicarboxy-diphenyl disulphide. Acyl groups Y$_5$ are preferably acyl groups derived from organic carboxylic acids, such as substituted or unsubstituted benzoyl groups or in particular lower alkanoyl, for example benzoyl or acetyl. A dicarboxylic acid of the formula XVII (Y$_5$ is carboxyl) is preferably in the form of the tautomeric hydroxymaleic acid. Compounds of the formula XVII which can be used are in particular pyruvic acid, acetylpyruvic acid and hydroxymaleic acid.

The treatment with a mineral acid is effected in a conventional manner, preferably by the brief action, for example an action of not more than two hours and preferably of about 30 to 60 minutes, of substantially concentrated sulphuric acid, such as commercially available concentrated sulphuric acid, preferably at about 25°–50° C. and in particular at about 30°–35° C.

The starting materials of the formulae XVI and XVII are known or, if they are new, can be prepared according to methods known per se.

A compound of the formula I which is obtainable according to the invention can be converted into another compound of the formula I in a manner known per se.

Thus, in a compound of the formula I in which Z is hydroxyl, the latter can be etherified in a conventional manner, for example methylated with dimethyl sulphate, or acylated for example with an acid anhydride, ketene or acid halide. Likewise, in compounds of the formula I in which R is hydroxyl, the latter can be converted into a substituted or unsubstituted lower alkoxy group, by etherification processes known per se. Thus, a carboxyl group of the formula —C(=O)—R (Ib) can be esterified, for example by treatment with a substituted or unsubstituted diazo-lower alkane or with a substituted or unsubstituted lower alkanol, in the presence of an acid, such as a mineral acid, for example hydrochloric acid or sulphuric acid, or of a suitable condensing agent, such as a dehydrating agent, for example di-cyclocarbodiimide, or, in order to form a hydroxy-lower alkyl ester, with an epoxy-lower alkane, for example ethylene oxide. Furthermore, a compound of the formula I in which a free carboxyl group of the formula Ib is in the form of a salt, for example in the form of an alkali metal salt, such as the sodium salt, can be reacted with a reactive ester of a substituted or unsubstituted lower alkanol, with, for example, a strong acid, such as a corresponding lower alkyl halide, for example lower alkyl chloride, bromide or iodide, or di-lower alkyl sulphate, or a compound of the formula I in which a free carboxyl group of the formula Ib is in the form of an anhydride, preferably in the form of a halogenocarbonyl group, for example the chlorocarbonyl group, which can be obtained, for example, by treating a compound of the formula I in which R is hydroxyl with a halogenating agent, for example thionyl chloride, can be reacted with a substituted or unsubstituted metal lower alkanolate, such as a corresponding alkali metal alkanolate, for example sodium alkanolate or potassium alkanolate, or with a substituted or unsubstituted lower alkanol in the presence of an acid-binding base, and compounds of the formula I in which R is substituted or unsubstituted lower alkoxy can thus be obtained. Substituents can be in a functionally modified form in an esterifying reagent and then set free in a compound of the formula I in which R is substituted lower alkoxy, in which substituents are in a functionally modified form. Thus, for example, 2,3-epoxypropyl chloride can be used as the esterifying reagent and the 2,3-epoxypropyl grouping in the resulting ester can subsequently be hydrolysed to the desired 2,3-dihydroxypropyl grouping.

In a compound of the formula I in which R is substituted or unsubstituted lower alkoxy, the latter can be converted into another substituted or unsubstituted lower alkoxy group by transesterification, for example by treatment with a substituted or unsubstituted lower alkanol in the presence of a suitable transesterification catalyst, such as a substituted or unsubstituted alkali metal lower alkanolate compound, for example a sodium or potassium lower alkanolate compound.

In a compound of the formula I, an esterified carboxyl group of the formula —C(=O)—R (Ib), in which R is a substituted or unsubstituted lower alkoxy group, can be converted into a free carboxyl group of the formula Ib in which R is hydroxyl in a conventional manner, for example by hydrolysis, customarily in an alkali medium, for example by treatment with water in the presence of an alkali metal hydroxide or alkaline earth metal hydroxide, for example sodium hydroxide.

Resulting free compounds of the formula I in which R is hydroxyl can be converted into salts in a manner known per se, inter alia by treatment with a base or with a suitable salt of a carboxylic acid, usually in the presence of a solvent or diluent.

Resulting salts can be converted into the free compounds in a manner known per se, for example by treatment with an acid reagent, such as a mineral acid.

The compounds, including their salts, can also be obtained in the form of their hydrates, or can incorporate the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process according to which a compound obtainable as an intermediate at any process stage is used as the starting material and the missing process steps are carried out, or according to which a starting material is formed under the reaction conditions or is used in the form of a derivative thereof, if desired in the form of a salt.

The starting materials used in the process of the present invention are preferably those which result in the compounds described initially as being particularly valuable. Novel starting materials and novel intermediates and processes for their preparation also constitute a subject of the present invention.

The present invention also relates to pharmaceutical compositions which contain compounds of the formula I or pharmaceutically acceptable salts thereof. The pharmaceutical compositions according to the invention are inhalation or insufflation compositions or those which are intended for enteral, such as oral or rectal, and parenteral administration to warm-blooded animals and which contain the pharmacological active ingredient on its own or together with a pharmaceutically acceptable carrier. The dosage of the active ingredient depends on the species of warm-blooded animal, the age and the individual condition and on the mode of administration.

The novel pharmaceutical compositions contain, for example, from about 10% to about 95%, preferably from about 20% to about 90%, of the active ingredient. Pharmaceutical compositions according to the invention are, for example, those in a form suitable for inhalation or insufflation, such as an aerosol or spray form, or in the form of dosage units, such as sugar-coated tablets, tablets, capsules or suppositories, and also ampoules.

The pharmaceutical compositions of the present invention are prepared in a manner known per se, for example by conventional mixing, granulating, sugar-coating, dissolving or lyophilising methods. Thus, pharmaceutical compositions for oral use can be obtained by combining the active ingredient with solid carriers, optionally granulating a resulting mixture, and processing the mixture or granules, if desired or necessary after the addition of suitable adjuncts, to tablets or sugar-coated tablet cores.

Suitable carriers are in particular fillers, such as sugar, for example lactose, sucrose, mannitol or sorbitol, cellulose preparations and/or calcium phosphates, for example tricalcium phosphate or calcium hydrogen phosphate, also binders, such as starch pastes, for example maize, corn, rice or potato starch paste, gelatin, tragacanth, methylcellulose and/or polyvinylpyrrolidone, and/or, if desired, disintegrators, such as the above starches, also carboxymethyl starch, crosslinked polyvinylpyrrolidone, agar, alginic acid or a salt thereof, such as sodium alginate. Adjuncts are chiefly glidants and lubricants, for example silicic acid, talc, stearic acid or salts thereof, such as magnesium stearate or calcium stearate, and/or polyethylene glycol. Sugar-coated tablet cores are previded with suitable coatings which can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or the coatings of sugar-coated tablets, for example to identify or indicate different doses of active ingredient.

Further pharmaceutical compositions for oral administration are dry-filled capsules and also soft-sealed capsules made from gelatin and a plasticiser, such as glycerol or sorbitol. The dry-filled capsules can contain the active ingredient in the form of granules, for example in admixture with fillers, such as lactose, binders, such as starches, and/or lubricants, such as talc or magnesium stearate, and optionally stabilisers. In soft capsules, the active ingredient is preferably dissolved or suspended in suitable liquids, such as fatty oils, paraffin oil or liquid polyethylene glocols, to which stabilisers can also be added.

Pharmaceutical compositions for rectal administration are, for example, suppositories, which consist of a combination of the active ingredient with a suppository base. Examples of suitable suppository bases are natural or synthetic tri-glycerides, paraffin hydrocarbons, polyethylene glycols or higher alkanols. Gelatin rectal capsules, which consist of a combination of the active ingredient with a base material, can also be used; base materials which can be used are, for example, liquid triglycerides, polyethylene glycols or paraffin hydrocarbons.

Suitable compositions for parenteral administration are, in particular, aqueous solutions of an active ingredient in a water-soluble form, for example of a water-soluble salt, and also suspensions of the active ingredient, such as corresponding oily injection suspensions, in which case suitable lipophilic solvents or vehicles, such as fatty oils, for example sesame oil, or synthetic fatty acid esters, for example ethyl oleate or tri-glycerides, are used, or aqueous injection suspensions which contain substances which increases the viscosity, for example sodium carboxymethylcellulose, sorbitol and/or dextran, and can also contain stabilisers.

Inhalation or insufflation compositions for the treatment of the respiratory passages by nasal or buccal administration are, for example, insufflation capsules which allow the active ingredient to insufflate in the form of a powder with the respiratory air, or aerosols or sprays which can disperse the pharmacological active ingredient in the form of a powder or in th form of drops of a solution or suspension. Compositions having powder-dispersing properties usually contain adjuncts in addition to the active ingredient, insufflation capsules containing, for example, solid carriers, such as lactose, and aerosol or spray compositions containing, for example, a liquid propellant gas having a boiling point below room temperature and also, if desired, further carriers, such as liquid or solid non-ionic or anionic surfactants and/or solid diluents. Compositions in which the pharmacological active ingredient is in solution contain, in addition to this ingredient, a suitable propellant, and also, if necessary, an additional solvent and/or a stabiliser. Compressed air can also be used in place of the propellant gas and in this case this compressed air can be produced as required by means of a suitable compression and pressure-release device.

Pharmaceutical compositions for topical and local use are, for example, lotions and creams, which contain a liquid or semi-solid oil-in-water or water-in-oil emulsion, and ointments (these preferably containing a preservative), for the treatment of the skin, eyedrops, which contain the active compound in aqueous or oily solution, and eye ointments, which preferably are produced in a sterile form, for the treatment of the eyes, powders, aerosols and sprays (similar to those described above for the treatment of the respiratory passages), and also coarse powders, which can be administered by rapid inhalation through the nostrils and nose drops, which contain the active compound in aqueous or oily solution, for the treatment of the nose, or lozenges which contain the active compound in a composition generally formed from sugar and gum arabic or tragacanth, to which flavourings can be added, and pastilles, which contain the active ingredient in an inert composition, for example consisting of gelatin and glycerol or sugar and gum arabic, for the local treatment of the mouth.

The invention also relates to the use of the novel compounds of the formula I and salts thereof as pharmacologically active compounds, especially as antiallergic agents, preferably in the form of pharmaceutical compositions. The daily dose which is administered to a warm-blooded animal weighing about 70 kg is from about 200 mg to about 1,200 mg.

The following examples illustrate the present invention without in any way restricting the scope thereof. The temperatures are in degrees Centigrade.

EXAMPLE 1

A mixture of 6.32 g of 2-[α-(methoxycarbonyl)-α-(4-methyl-piperazino)-methylene]-6-methyl-coumaranone and 190 ml of 6 N hydrochloric acid is stirred at room temperature, whereupon a crystalline precipitate forms; after 45 minutes the precipitate is filtered off and washed with water until neutral. After recrystallisation from a mixture of methylene chloride and petroleum ether with the addition of active charcoal, methyl 3-hydroxy-6-methyl-benzofuryl-2-glyoxylate is obtained; melting point 159°–160° C.

The starting material can be prepared, for example, as follows.

250 ml of 1,2-dichloroethane and 265 g of powdered anhydrous aluminium chloride are initially introduced into a stirred flask provided with a hydrogen chloride outlet. Subsequently, in the course of about 30 minutes, with stirring, 54 g of 3-methyl-phenol and then, in the course of 1.5 hours, 87.5 g of 2,3-dichloromaleic anhydride (95% pure) are added at 20°–30°. After stirring for a further 4 hours at room temperature (about 20°–25°) the reaction mixture is discharged into a mixture of 250 ml of concentrated hydrochloric acid, water and ice; end volume about 3,000 ml. The dichloroethane solution is separated off, 500 ml of water are added and the organic solvent is removed under reduced pressure in a rotary evaporator at a heating bath temperature of about 50°. The residue is dissolved in 3,000 ml of water with the addition of 200 ml of a 30% strength solution of sodium hydroxide in water, the solution is stirred for 10 minutes at 20°–25° and is then clarified by filtration, using a silica gel filter aid. The reaction product is precipitated from the filtrate at 0°–5° by adding excess hydrochloric acid and is filtered off and washed with a little water. After drying at 60° and under reduced pressure, reddish-tinged yellow 2-carboxychloromethylene-6-methyl-coumaranone is obtained and after recrystallisation from ethyl acetate this melts at 172°–174°.

A suspension of 120 g of 2-carboxychloromethylene-6-methyl-coumaranone in 600 ml of water is neutralised to a pH value of 7.0 by slowly adding an aqueous solution of sodium hydroxide, and 150 ml of dimethyl sulphate are added dropwise at 20°–25° in the course of 5 hours, the pH value being kept between 6.5 and 7.0 by the continuous addition of an approximately 10% strength aqueous solution of sodium carbonate, with stirring. The product is then filtered off, washed with water and dried under reduced pressure at 60°. This gives 2-methoxycarbonylchloromethylene-6-methyl-coumaranone, which according to chromatography is a single compound and which after recrystallisation from ethanol melts at 120°–121°. Unchanged pure starting material can be recovered from the aqueous filtrate by precipitating with hydrochloric acid and can be re-used.

20 g of 1-methyl-piperazine are added dropwise to a suspension of 25.25 g of 2-methoxycarbonyl-chloromethylene-6-methyl-coumaranone in 500 ml of methanol, with stirring, at an internal temperature of 15°–20°. The mixture is stirred for a further 3 hours at room temperature and the volatile constituents are then completely evaporated off under reduced pressure. 150 ml of water and 250 ml of diethyl ether are added to the oily residue, the mixture is shaken well until two clear layers form, the ether phase is separated from the aqueous fraction and the latter is extracted a further four times with diethyl ether. The combined organic phases are washed three times with water, dried over sodium sulphate and concentrated to a smaller volume under reduced pressure. 2-[α-(Methoxycarbonyl)-α-(4-methyl-piperazino)-methylene]-6-methyl-coumaranone is obtained on grinding and after recrystallisation from hot cyclohexane this melts at 118°–120°.

EXAMPLE 2

A solution of 37.2 g of 2-(α-dimethylaminoα-methoxy-carbonyl-methylene)-6-methyl-coumaranone in 1,000 ml of 6 N hydrochloric acid is stirred at room temperature. After 2 hours the product which has precipitated is filtered off and washed with water until neutral and the dried crude product is recrystallised from ethyl acetate. This gives methyl 3-hydroxy-6-methyl-benzofuryl-2-glyoxylate which has a melting point of 159°–161° and is identical to the product of Example 1.

The starting material can be prepared as follows:

33 g of a 33% strength ethanolic solution of dimethylamine is added all at once, with stirring, to a suspension of 20.2 g of 2-methoxycarbonyl-chloromethylene-6-methyl-coumaranone in 800 ml of absolute ethanol. The mixture is then stirred for a further 3 hours at room temperature. After the reaction has ended, the reaction mixture is concentrated to a small volume under reduced pressure, after which 2-(α-dimethylamino-α-methoxycarbonyl-methylene)-6-methyl-coumaranone crystallises out on grinding with a little water. After recrystallisation from a mixture of methylene chloride and petroleum ether, the product melts at 137°–139°.

EXAMPLE 3

16 g of 4-methyl-piperazine are added all at once to a suspension of 9.55 g of 2-carboxychloromethylene-6-methyl-coumaranone in 250 ml of isopropanol, at room temperature, with stirring, and the mixture is stirred for a further 16 hours at room temperature. After evaporating the volatile constituents under reduced pressure, the residual resin, which contains 2-[α-carboxy-α-(4-methyl-piperazino)-methylene]-6-methyl-coumaranone, is dissolved in 150 ml of warm water, the solution is filtered with active charcoal and the filtrate is carefully rendered strongly acid with concentrated hydrochloric acid, with ice-cooling. An oily product precipitates out and this soon crystallises on grinding. This gives 3-hydroxy-6-methyl-benzofuryl-2-glyoxylic acid, which after recrystallisation from a mixture of dimethylformamide and water melts at 224°–226°.

EXAMPLE 4

After standing for 18 hours, a clear solution of 0.234 g of methyl 3-hydroxy-6-methyl-benzofuryl-2-glyoxylate in 20 ml of 0.1 N aqueous solution of sodium hydroxide, which has been prepared at room temperature, is rendered strongly acid with 2 N hydrochloric acid. The product which has precipitated is filtered off and washed with water until neutral and 3-hydroxy-6-methyl-benzofuryl-2-glyoxylic acid is thus obtained; melting point 225° (decomposition).

EXAMPLE 5

54 g of guanidine carbonate are added slowly to a suspension of 71.6 g of 2-carboxychloromethylene-5-methyl-coumaranone in 500 ml of glacial acetic acid. The reaction mixture is kept at 60° to 65° for 16 hours, with stirring, and is then cooled to room temperature, 200 ml of water are added and the product which has separated out is filtered off. This product is heated briefly to the boil in a mixture of 350 ml of ethanol and 350 ml of water and 200 ml of concentrated hydrochloric acid are added. The crystalline material is filtered off and washed with water. After drying under reduced pressure at 60° this gives 3-hydroxy-5-methyl-benzofuryl-2-glyoxylic acid; melting point 239° (with decomposition).

The starting material can be prepared by the procedure described in Example 1; after recrystallisation from ethylene glycol dimethyl ether, the 2-carboxychloromethylene-5-methyl-coumaranone prepared using 4-methyl-phenol melts at 197°.

EXAMPLE 6

A mixture of 30 g of 2-(α-dimethylamino-α-methoxycarbonyl-methylene)-5-methyl-coumaranone and 200 ml of 2 N sulphuric acid is stirred for one hour at 60°; the precipitate is filtered off, washed with water and dried under reduced pressure at 60°. This gives methyl 3-hydroxy-5-methyl-benzoofuryl-2-glyoxylate; melting point 148°–149°.

The starting material can be prepared as follows:

A mixture of 50.6 g of 2-methoxycarbonyl-chloromethylene-5-methyl-coumaranone (melting point 74°–81° after recrystallisation from ethanol), 600 ml of ethanol and 18 g of dimethylamine (in the form of an approximately 40% strength aqueous solution) is stirred at 20° to 30° for 1½ hours and then diluted with a little water. The ethanol is distilled off in a rotary evaporator under reduced pressure and the residual mixture is filtered. The filter residue is dried and gives 2-(α-dimethylamino-α-methoxycarbonylmethylene)-5-methyl-coumaranone; melting point 127°–129°.

EXAMPLE 7

A mixture of 6.0 g of 2-carboxychloromethylene-5-methyl-coumaranone in 20 ml of dimethylsulphoxide and 5 ml of water is stirred for 75 minutes at 60° and then diluted with ice-water. The resulting precipitate is filtered off, washed with water and dried. This gives 3-hydroxy-5-methyl-benzofuryl-2-glyoxylic acid which has a melting point of 239° (with decomposition) and is identical to the product of the procedure according to Example 5.

EXAMPLE 8

A mixture of 30 g of 3-hydroxy-5-methyl-benzofuryl-2-glyoxylic acid, 250 ml of pure methanol and 0.6 ml of concentrated sulphuric acid is refluxed for two hours. The reaction mixture is added dropwise to ice-water (volume: about 1,500 ml), the resulting mixture is neutralised to pH 7 with an aqueous solution of sodium carbonate and filtered and the filter residue is dried at 60° under reduced pressure. This gives methyl 3-hydroxy-5-methyl-benzofuryl-2-glyoxylate, which after recrystallisation from methanol melts at 150°–151°.

EXAMPLE 9

A solution of 16.4 g (0.1 mol) of 5-methoxy-3(2H)-benzofuranone (5-methoxycoumaranone) and 14.6 g of diethyl oxalate in 400 ml of absolute diethyl ether is added dropwise in the course of ½ an hour to a solution of 2.3 g pof sodium in 50 ml of absolute ethanol and 100 ml of absolute diethyl ether, at 20°, with stirring. The mixture is then stirred for a further one hour and the resulting precipitate is filtered off and washed with ether. The precipitate is dissolved in water and 50 ml of 2 N sulphuric acid are added dropwise at 0°, with stirring. Thereupon ethyl 3-hydroxy-5-methoxy-benzofuryl-2-glyoxylate precipitates out and this is obtained in the pure form after filtering off with suction, washing with water and recrystallising from tetrahydrofurane. Melting point: 150°–152°.

EXAMPLE 10

20.6 g (0.065 mol) of 5-methyl-2-(α-piperidino-α-carbomethoxy-methylene)-thioindoxyl are refluxed in 325 ml of 5% strength sulphuric acid for one hour. After cooling, the yellow crystals are filtered off with suction and dried at 60° and 100 mm Hg. This gives methyl 3-hydroxy-5-methyl-[2H]-benzothienyl-2-glyoxylate, which when recrystallised from 10% strength methanolic sulphuric acid gives yellow crystals having a melting point of 153°–154°.

The starting material can be prepared as follows:

66.8 g (0.4 mol) of dichloromaleic anhydride and 23.5 g (0.22 mol) of anhydrous sodium acetate in 300 ml of ethylene glycol dimethyl ether are initially introduced into a stirred flask and 24.8 g (0.2 mol) of p-thiocresol in 300 ml of ethylene glycol dimethyl ether are added dropwise at 50° in the course of 2 hours. Within this period, the temperature is also raised step-wise to 70°. The reaction mixture is then stirred at this temperature for 16 hours. The sodium chloride which has precipitated is separated off and the filtrate is evaporated. A viscous red oil is obtained. This is added dropwise in the course of 1½ hours to a suspension of 100 g (0.76 mol) of aluminium chloride in 100 ml of 1,2-dichloroethane, which is kept at 0°–10° by means of an ice bath. After stirring for one hour at room temperature, the reaction mixture is poured onto 800 g of ice, the aqueous phase is decanted off and 50 ml of ethyl acetate are added to the red oily product, whereupon crystallisation starts. After stirring for one and a half hours, crude 5-methyl-2-carboxychloromethylene-thioindoxyl is separated off and dried at 60°/100 mm Hg. For purification, these crystals are suspended in 190 ml of ethyl acetate and the suspension is heated to the boil, immediately cooled again and filtered with suction. After drying, red crystals having a melting point of 176°–178° are obtained. The crude product can be used for further reactions.

24.4 g (0.095 mol) of 2-carboxychloromethylene-5-methylthioindoxyl in 213 ml of 10% strength methanolic sulphuric acid are heated to the boil for 2 hours. After cooling, the orange crystals are filtered off with suction and washed twice with, in each case, 125 ml of a saturated solution of sodium bicarbonate and once with 100 ml of water. After drying at 60°/100 mm Hg, this gives 2-methoxycarbonyl-chloromethylene-5-methyl-thioindoxyl in the form of orange crystals having a melting point of 208°. Further crystals can be obtained from the mother liquor.

42 g (0.154 mol) of 2-methoxycarbonylchloromethylene-5-methyl-thioindoxyl are suspended in 700 ml of ethanol and 37.8 g (0.42 mol) of piperidine are added at 20°–25° C. After stirring for 3 hours at 20°–25°, the reaction mixture is poured onto 500 g of ice and the crystals which have precipitated are filtered off. Recrystallisation from ethyl acetate gives 2-(α-methoxycarbonyl-α-piperidino-methylene)-5-methyl-thioindoxyl in the form of orange-yellow crystals having a melting point of 118°–120°.

Methyl 3-hydroxy-6-methyl-[2H]benzothienyl-2-glyoxylate having a melting point of 153°–155° can be prepared analogously, via 6-methyl-2-(α-morpholino-α-carbomethoxy)-methylene-thioindoxyl.

EXAMPLE 11

10.7 g (0.04 mol) of 2-methoxycarbonyl-chloromethylene-6-methyl-thioindoxyl having a melting point of 214°–216° (decomposition), which is obtainable from m-thiocresol in a manner analogous to that described in Example 1, are suspended in 35 ml of ethanol, and 6.8 g (0.08 mol) of piperidine in 15 ml of ethanol are added at 20°–25° in the course of 20 minutes. After stirring for two hours at 20°–25°, 70 ml of 10% strength sulphuric acid are added dropwise in the course of 40 minutes, with ice-cooling. After stirring thoroughly for three hours, the reaction mixture is filtered with suction and the material on the filter is dried; this gives methyl 3-hydroxy-6-methyl[2H]-benzothienyl-2-glyoxylate, which after recrystallisation from ethyl acetate melts at 153°–155°.

EXAMPLE 12

The following compounds can also be prepared in a manner analogous to that described in Examples 1–11:
methyl 3-hydroxy-benzofuranyl-2-glyoxylate having a melting point of 135°–137°, starting from 2-[α-methoxycarbonyl-α-(N-methylpiperazino)-methylene]-coumaranone having a melting point of 125°–127°; methyl 3-hydroxy-6-methoxy-benzofuranyl-2-glyoxylate having a melting point of 172°–173°, starting from 6-methoxy-2-[α-methoxycarbonyl-α-(N-methylpiperazino)-methylene]-coumaranone maleate having a melting point of 188°–190°; methyl 5,6-dimethyl-3-hydroxy-benzofuranyl-2-glyoxylate having a melting point of 172°–173°, starting from 5,6-dimethyl-2-[α-methoxycarbonyl-α-(N-methylpiperazino)-methylene]-coumaranone having a melting point of 140°–142°; methyl 5,7-dimethyl-3-hydroxy-benzofuranyl-2-glyoxylate having a melting point of 136°–136°, starting from 5,7-dimethyl-2-[α-methoxycarbonyl-α-α-(4-methylpiperazino)-methylene]-coumaranone having a melting point of 136°–138°; methyl 3-hydroxy-6-methyl-5-nitro-benzofuranyl-2-glyoxylate having a melting point of 208°–211°, starting from 2-[α-methoxycarbonyl-α-(N-methylpiperazino)-methylene]-6-methyl-5-nitro-coumaranone having a melting point of 151°–153°; ethyl 3,6-dihydroxy-benzofuranyl-2-glyoxylate having a melting point of 216°–218° (decomposition), starting from 5 g of 6-hydroxy-2-[α-ethoxycarbonyl-α-(N-methylpiperazino)-methylene]-coumaranone having a melting poing of 208°–209°; and 2-hydroxy-ethyl 3-hydroxy-6methyl-benzofuranyl-2-glyoxylate having a melting point of 133°–135°, starting from 5.1 g of 2-[α-(2-hydroxyethoxycarbonyl)-α-(N-methylpiperazino)-methylene]-6-methyl-coumaranone having a melting point of 157°. The starting materials in each case can be obtained analogously to the procedure indicated in Example 1, the correspoinding phenol or thiophenol and 2,3-dichloromaleic anhydride giving the corresponding 2-carboxychloromethylenecoumaranone, the latter being esterified and the reaction product being further reacted with N-methylpiperazine.

EXAMPLE 13

A mixture of 10.7 g of 2-(α-methoxycarbonyl-α-piperidinomethylene)-5,6-trimethylene-coumaranone and 340 ml of 6 N hydrochloric acid is stirred at room temperature for 3 hours. The crystalline precipitate is filtered off with suction and taken up in chloroform. The chloroform solution is washed with water, dried and evaporated. The residue thus obtained is recrystallised from ethyl acetate and this gives methyl 3-hydroxy-5,6-trimethylene-benzofuranyl-2-glyoxylate having a melting point of 189°–191°.

The starting material, i.e. 2-(α-methoxycarbonyl-α-piperidino-methylene)-5,6-trimethylene-coumaranone, is prepared analogously to Example 1 by reacting 3,4-trimethylenephenol with 2,3-dichloromaleic anhydride to give 2-carboxychloromethylene-5,6-trimethyl-coumaranone, further reacting the latter with dimethyl sulphate to give 2-methoxycarbonylchloromethylene-5,6-trimethylene-coumaranone having a melting point of 113°–114° and reacting this with piperidine. The compound melts at 112°–123°.

EXAMPLE 14

3-Hydroxy-5,6-trimethylene-benzothienyl-2-glyoxylic acid, having a melting point of 220°–223° (decomposition), and the methyl ester thereof, having a melting point of 206°–208° (from methyl acetate) can be prepared in a manner analogous to that described in Example 10, starting from dichloromaleic anhydride and 3,4-trimethylene-thiophenol via 2-carboxychloromethylene-5,6-trimethylene-thioindoxyl or 2-(α-methoxycarbonylchloromethylene)-5,6-trimethylene-thioindoxyl by reaction with piperidine and subsequent treatment of the reaction product with 10% strength sulphuric acid.

EXAMPLE 15

Tablets containing 0.1 g of active ingredient, for example methyl 3-hydroxy-5-methyl-benzofuryl-2-glyoxylate or methyl 3-hydroxy-5-methyl-benzothienyl-2-glyoxylate, are prepared as follows:

Composition (for 1,000 tablets):

| Active ingredient | 100.00 g |
|---|---|
| Lactose | 50.00 g |
| Corn starch | 73.00 g |
| Colloidal silica | 13.00 g |
| Magnesium stearate | 2.00 g |
| Talc | 12.00 g |
| Water | q.s. |

The active ingredient is mixed with a portion of the corn starch and with the lactose and the colloidal silica and the mixture is forced through a sieve. A further portion of the corn starch is mixed to a paste with five times the amount of water on a water bath and the above powder mixture is kneaded with this paste until a slightly plastic mass has formed. The plastic mass is prepared through a sieve of about 3 mm mesh width and dried and the dry granules are again forced through a sieve. The remaining corn starch, the talc and the magnesium stearate are then mixed in and the resulting mixture is compressed to tablets of 0.25 g.

EXAMPLE 16

An approximately 2% strength aqueous solution, which is suitable for inhalation, of an active ingredient according to the invention which is water-soluble in the free form or in the form of the sodium salt can be prepared, for example, in the following composition:

Composition:

| Active ingredient, for example sodium 3-hydroxy-methyl-benzofuryl-2-glyoxylate | 2,000 mg |
|---|---|
| Stabiliser, for example the disodium salt of ethylenediaminetetraacetic acid | 10 mg |
| Preservative, for example benzalkonium chloride | 10 mg |
| Water, freshly distilled | To make up to 100 ml |

Preparation:

The active ingredient is dissolved in freshly distilled water with the addition of the equimolecular amount of 2 N sodium hydroxide solution. The stabiliser and the preservative are then added. After all of the components have dissolved completely, the resulting solution is made up to 100 ml and filled into small bottles and these are sealed gas-tight.

EXAMPLE 17

Capsules which are suitable for insufflation and contain about 25 mg of an active ingredient according to the invention can be prepared, for example, in the following composition:

Composition:

| Active ingredient, for example methyl 3-hydroxy-5,6-trimethylene-benzofuryl-2-glyoxylate or methyl 3-hydroxy-5-methyl-benzothienyl-2-glyoxylate | 25 mg |
|---|---|
| Lactose, very finely ground | 25 mg |

Preparation:

The active ingredient and the lactose are intimately mixed. The resulting powder is then sieved and filled in 50 mg portions into 1,000 gelatin capsules.

EXAMPLE 18

Corresponding pharmaceutical compositions containing another of the compounds of the general formula I described in Examples 1–14 can be prepared in a manner analogous to that described in Examples 15–17.

What is claimed is:

1. A compound of the formula

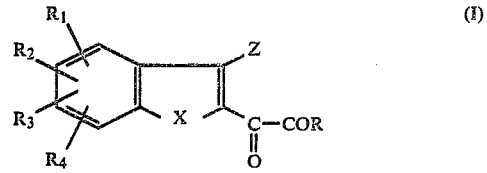

in which Z is free or lower alkanoyloxy, X is thio or oxy, R is hydroxyl, hydroxy-lower alkoxy or lower alkoxy-lower alkoxy in which the two oxygen atoms are separated by 2 or 3 carbon atoms, $R_1$ is lower alkyl, cycloalkyl having 5 to 8 ring members, hydroxyl, lower alkoxy, phenoxy, phenoxy substituted by lower alkyl, lower alkoxy, halogen and/or nitro, amino, N-mono- or N,N-di-lower alkylamino, N-lower alkanoylamino, lower alkanoyl, benzoyl, benzoyl substituted by lower alkyl, lower alkoxy, halogen and/or nitro, carboxyl, halogen, nitro or, if Z is lower alkanoyloxy and/or X is oxy, hydrogen, $R_2$ is hydrogen, lower alkyl, hydroxyl or halogen and $R_3$ and $R_4$ are each hydrogen or lower alkyl with the proviso that $R_1$ is different from methyl bound in the 4-position when $R_2$ denotes methyl bound in 6-position, $R_3$ and $R_4$ are hydrogen, X denotes oxy and R represents ethoxy, or in which two adjacent radicals $R_1$, $R_2$, $R_3$ and $R_4$ together form lower alkylene having 3 to 5 chain carbon atoms or 1,4-butadienylene and the other two radicals are each hydrogen, or a pharmaceutically acceptable salt thereof.

2. A compound of the formula I as claimed in claim 1, in which R is hydroxyl, lower alkoxy having not more than 4 carbon atoms, hydroxy-lower alkoxy having not more than 4 carbon atoms, in which the two oxygen atoms are separated by 2 to 3 carbon atoms, or lower alkoxy-lower alkoxy having not more than 7 carbon atoms, in which the two oxygen atoms are separated by 2 to 3 carbon atoms, $R_1$ is lower alkyl having not more than 4 carbon atoms, cyclohexyl, hydroxyl, lower alkoxy having not more than 4 carbon atoms, carboxyl, lower alkanoyl, lower alkanoylamino, N,N-di-lower alkyl-amino, halogen having an atomic number of not more than 35, nitro or, if Z is lower alkanoyloxy and/or X is oxy, hydrogen, and $R_2$ is hydrogen, lower alkyl having not more than 4 carbon atoms or halogen having an atomic number of not more than 35 and $R_3$ and $R_4$ are each hydrogen or lower alkyl having not more than 4 carbon atoms, or two of the radicals $R_1$, $R_2$, $R_3$ and $R_4$ together form lower alkylene having 3 to 5 chain carbon atoms and are a substituent in the 5- and 6-positions or form 1,4-butadienylene and are a substituent in the 4- and 5-positions, and the other two radicals are hydrogen, or a pharmaceutically acceptable salt thereof.

3. A compound as claimed in claim 1 of the formula

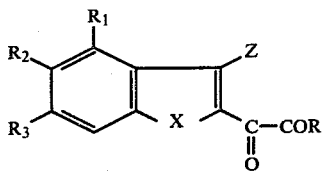

(Ia)

in which Z is hydroxy or lower alkanoyloxy having not more than 4 carbon atoms, X is thio or oxy, R is hydroxyl, lower alkoxy having not more than 4 carbon atoms, hydroxy-lower alkoxy having not more than 4 carbon atoms, in which the two oxygen atoms are separated by 2 to 3 carbon atoms, or lower alkoxy-lower alkoxy having not more than 4 carbon atoms, in which the two oxygen atoms are separated by 2 to 3 carbon atoms, $R_1$ denotes hydrogen or lower alkyl having not more than 4 carbon atoms, $R_2$ denotes hydrogen, lower alkyl having not more than 4 carbon atoms or nitro, $R_3$ denotes hydrogen, lower alkyl having not more than 4 carbon atoms, hydroxy or lower alkoxy having not more than 4 carbon atoms, and only one of $R_2$ and $R_3$ differs from hydrogen or lower alkyl, or $R_1$ is hydrogen and $R_2$ and $R_3$ together are 1,3-propylene, with the proviso that at least one of the radicals $R_1$, $R_2$ and $R_3$ differs from hydrogen when X is thio and R is hydroxyl and $R_1$ differs from methyl when $R_3$ denotes methyl, $R_2$ denotes hydrogen, X denotes oxy and R denotes ethoxy, or a pharmaceutically acceptable salt thereof.

4. A compound as claimed in claim 1 being methyl 3-hydroxy-6-methyl-benzofuryl-2-glyoxylate.

5. A compound as claimed in claim 1 being methyl 3-hydroxy-5,6-trimethylene-benzofuryl-2-glyoxylate.

6. A compound as claimed in claim 1 being methyl 3-hydroxy-5-methyl-[2H]benzothienyl-2-glyoxylate.

7. A compound as claimed in claim 1 being methyl 3-hydroxy-6-methyl-[2H]benzothienyl-2-glyoxylate.

8. A compound as claimed in claim 1 being methyl 3-hydroxy-5,6-trimethylene-[2H]benzothienyl-2-glyoxylate.

9. A compound as claimed in claim 1 being 3-Hydroxy-5,6-trimethylene-[2H]benzothienyl-glyoxylic acid or a pharmaceutically acceptable salt, thereof.

10. A pharmaceutical composition comprising an anti-allergically effective amount of a compound as claimed in claim 1 together with a pharmaceutically acceptable carrier and/or adjuncts.

* * * * *